United States Patent [19]
Litchman

[11] Patent Number: 5,142,910
[45] Date of Patent: Sep. 1, 1992

[54] DYNAMIC PHYSIOLOGICAL FUNCTION TESTING APPARATUS AND METHOD

[75] Inventor: Henry M. Litchman, Providence, R.I.

[73] Assignee: Occupational Orthopaedic Systems, Inc., Pawtucket, R.I.

[21] Appl. No.: 544,744

[22] Filed: Jun. 27, 1990

[51] Int. Cl.$^5$ .............................................. A61B 5/22
[52] U.S. Cl. ..................................................... 73/379
[58] Field of Search ................. 73/865.4, 862.03, 379; 310/93; 180/19.1–19.3; 280/79.11, 47.35; 272/93, 68, 70.3, 128–130; 128/774, 782; 346/8

[56] References Cited

U.S. PATENT DOCUMENTS

| | | | |
|---|---|---|---|
| 2,607,996 | 8/1952 | Moyer | 280/47.35 |
| 2,644,334 | 7/1953 | Perry | 73/379 |
| 3,749,893 | 7/1973 | Hileman | 346/8 |
| 3,786,422 | 1/1974 | Lubkin | 346/8 |
| 3,876,024 | 4/1975 | Shieman et al. | 180/19.1 |
| 3,897,060 | 7/1975 | Jennings | 273/55 R |
| 3,922,918 | 12/1975 | Farrar, Jr. | 73/379 |
| 3,972,238 | 8/1976 | Thatcher | 73/380 |
| 3,983,746 | 10/1976 | Phillips et al. | 346/8 |
| 3,989,240 | 11/1976 | Victor et al. | 272/125 |
| 4,169,666 | 10/1979 | Slater et al. | 352/133 |
| 4,451,307 | 5/1984 | O'Hare | 273/132 |
| 4,496,867 | 1/1985 | Marandet et al. | 310/93 |
| 4,565,368 | 1/1986 | Boettcher | 272/129 |
| 4,697,661 | 10/1987 | Pajerski et al. | 180/6.5 |
| 4,728,923 | 3/1988 | Finger | 340/671 |
| 4,788,463 | 11/1988 | Layh | 310/93 |
| 4,824,103 | 4/1989 | Smidt | 272/125 |
| 4,825,972 | 5/1989 | Shimizu | 364/424.01 |

OTHER PUBLICATIONS

Occupational Orthopedic Center, "B200 Back Evaluation System", 1988.

Baltimore Therapeutic Equipment Co., "BTE Work Simulator TM A Versatile evaluation and rehabilitation instrument".

J. C. Gilbert et al., "Simple Method to Determine Sincerity of Effort During a Maximal Isometric Test of Grip Strength", Amer. Jour. of Phys. Med., vol. 62, No. 3, Jun., 1983.

H. Krombholz, "On The Association of Effort and Force of Handgrip", Perceptual and Motor Skills, vol. 60, pp. 161–162, 1985.

B. R. Niebuhr et al., "Detecting Sincerity of Effort When Measuring Grip Strength", American Journal of Physical Medicine, vol., 66, No. 1, pp. 16–24, Feb. 1987.

G. A. Smith, "Assessing Sincerity of Effort in Maximal Grip Strength Tests", American Journal of Physical Medicine & Rehabilitation, vol. 68, No. 2, pp. 73–80, Apr., 1989.

K. H. E. Kroemer, "Evaluation of Maximal and Submaximal Static Muscle Exertions", Human Factor, vol. 23, No. 6, pp. 643–653, Oct., 1981.

(List continued on next page.)

*Primary Examiner*—Robert Raevis

[57] ABSTRACT

A cart for measuring dynamic physiological forces has a plurality of wheels, a handle, and a brake attached to at least one of the wheels for controlling the amount of force required to move the cart. A directional sensor indicates the direction in which the cart is moving, and a velocity sensor indicates the velocity of the cart. Grip sensors on the handle detect the gripping force applied to the handle. A force sensor between the handle and the cart indicates the amount of force applied to the handle to move the cart. Data loggers connected to sensors record indications from the sensors. A computer is connected to the data loggers for accepting the recorded indications. A method of using the cart for measuring dynamic muscle function includes presetting the brake for a known resistance to movement, having a test subject move the cart along a predetermined course, measuring the force required to move the cart, measuring the velocity of movement of the cart, and measuring the direction of the cart.

19 Claims, 6 Drawing Sheets

OTHER PUBLICATIONS

J. M. Stevenson et al., "Isoinertial Tests to Predict Lifting Performance", Ergonomics, vol. 32, No. 2, pp. 157-166, Feb. 1989.

F. Aghazadeh, "A Comparison of Dynamic- and Static-Strength Models for Prediction of Lifting Capacity", Ergonomics, vol. 28, No. 10, pp. 1409-1417, Oct., 1985.

I. Jacobs et al., "Comparison of Isokinetic and Isoinertial Lifting Tests As Predictors of Maximal Lifting Capacity", European Journal of Applied Physiology and Occupational Physiology, vol. 57, pp. 146-153, 1988.

K. H. E. Kroemer, "An Isoinertial Technique to Assess Individual Lifting Capability", Human Factors, vol. 25, No. 5, pp. 493-506, Oct., 1983.

A. Garg, "A Comparison of Isometric Strength and Dynamic Lifting Capability", Ergonomics, vol. 23, No. 1, pp. 13-27, Jan., 1980.

J. J. Knapik et al., "Isometric, Isotonic, and Isokinetic Torque Variations in Four Muscle Groups Through A Range of Joint Motion", Physical Therapy, vol. 63, No. 6, pp. 938-947, Jun., 1983.

B. C. Jiang, "Psychophysical Modeling of Manual Materials-Handling Capacities Using Isoinertial Strength Variables", Human Factors, vol. 28, No. 6, pp. 691-702, Dec., 1986.

DYNAMIC PHYSIOLOGICAL FUNCTION TESTING APPARATUS AND METHOD

BACKGROUND OF THE INVENTION

This invention relates to apparatus and methods for testing dynamic physiological functions.

Various methods and devices are used to determine a person's physical strength and ability to perform certain physical tasks. Such methods and devices are used in preemployment testing to determine a person's ability to perform certain employment related tasks, in injury evaluation related to workman's compensation claims, in rehabilitation exercise, in general exercise and physical conditioning, and in general injury evaluation. For example, Baltimore Therapeutic Equipment Co., Baltimore, Md., describes a stationery device and method which is said to effectively simulate the actual job task, or use muscle groups affected by injury, and record the subject's performance.

SUMMARY OF THE INVENTION

In general, in various aspects, this invention features a cart for measuring dynamic physiological forces. The cart includes a movable structure having wheels and a handle. A brake is attached to the front axle for controlling the amount of force required to move the cart. The related aspects include a directional sensor which indicates the direction in which the cart is moving; a velocity sensor which indicates the velocity of the cart; grip sensors on the handle to detect the gripping forces applied to the handle; and a force sensor between the handle and the cart which indicates the amount of force applied to the handle to move the cart.

In preferred embodiments of these aspects, the grip sensors are a pair of elongated beams spaced from and substantially parallel to the handle with a strain gauge attached between one end of the beam and the handle; the brake has a rotary portion connected to the axle and an adjacent fixed portion connected to the cart for applying a variable resistance to the free rotation of the rotary portion (one such brake is an electromagnetic brake responsive to the amount of electrical energy supplied to it); and the directional sensor includes a wheel contacting the surface on which the cart is moved connected by an angled member to the shaft of a cart-mounted potentiometer.

Other preferred embodiments further include data loggers connected to at least one, most preferably each, of the force, directional, velocity, and grip sensors for recording separately the indications from each of the sensors as functions of time; and a computer is connected to the data loggers for accepting the recorded indications.

In general, in various related aspects, the invention features a method of using the above-described cart for measuring dynamic muscle function. These methods include combinations of the following steps: presetting the brake for a known resistance to movement; having a test subject move the cart along a predetermined course; measuring the force required to move the cart, including individual grip force and overall push; measuring the velocity of movement of the cart; and measuring the direction of the cart. Moving the cart includes pushing, pulling and pushing while turning.

In another related aspect, the invention features a method which includes measuring the test subject for maximal isometric strength, and presetting the above-described resistance of the brake to some fraction of the measured maximal isometric strength. Preferably, the fraction is set between 20% and 60% of the measured maximal isometric strength.

In yet another related aspect, the method features a method which includes calculating one or more of the dynamic physiological forces required to move the cart from one or more of the force, velocity, and directional measurements; comparing the calculated dynamic physiological forces with prior calculations of the forces from the same or other test subjects; and determining the level of physiological function of said test subject from said comparison.

The invention provides a clinical tool and therapy test apparatus for measuring forces characteristic of dynamic physiological functions. The tool is stable, has variable mobility, is maneuverable, and is adaptable to anthropomorphic measurements of human functions. It accurately simulates actual pushing, pulling and turning tasks where a force is exerted against a constant or even a variable resistance. The mobility of the tool requires the user to use several large muscle groups rather than smaller isolated muscle groups; thus, providing a better estimate of overall muscle function than prior isometric or stationary tests. Measurements are not limited to incremental mass units, and fatigue is reduced since repeated trials are unnecessary to determine the maximum force the subject is able to exert against a given resistance.

DESCRIPTION OF THE PREFERRED EMBODIMENTS

A brief description of the drawings follows.

Drawings

STRUCTURE

Figure 1:
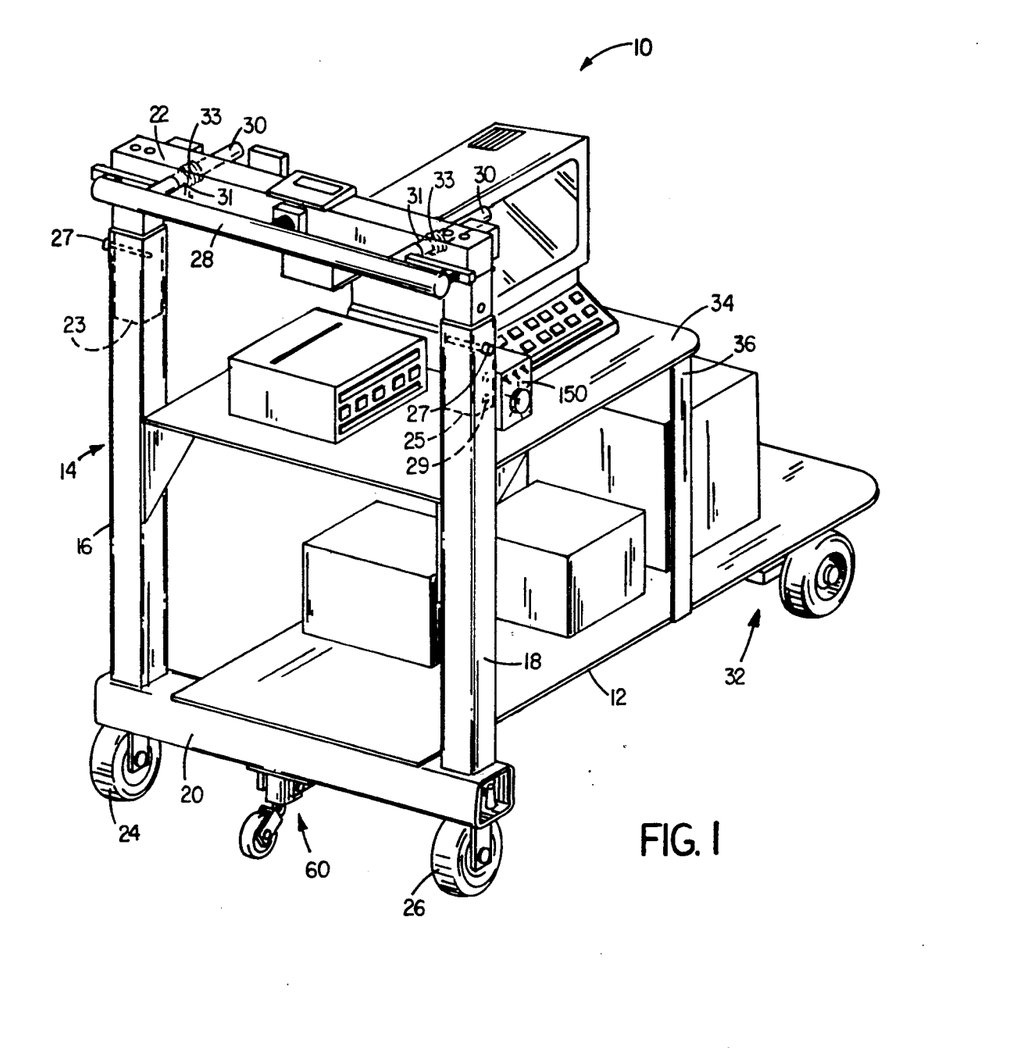
FIGS. 1, 2, and 3 are a perspective side, and front view of a cart, respectively.
Figure 2:
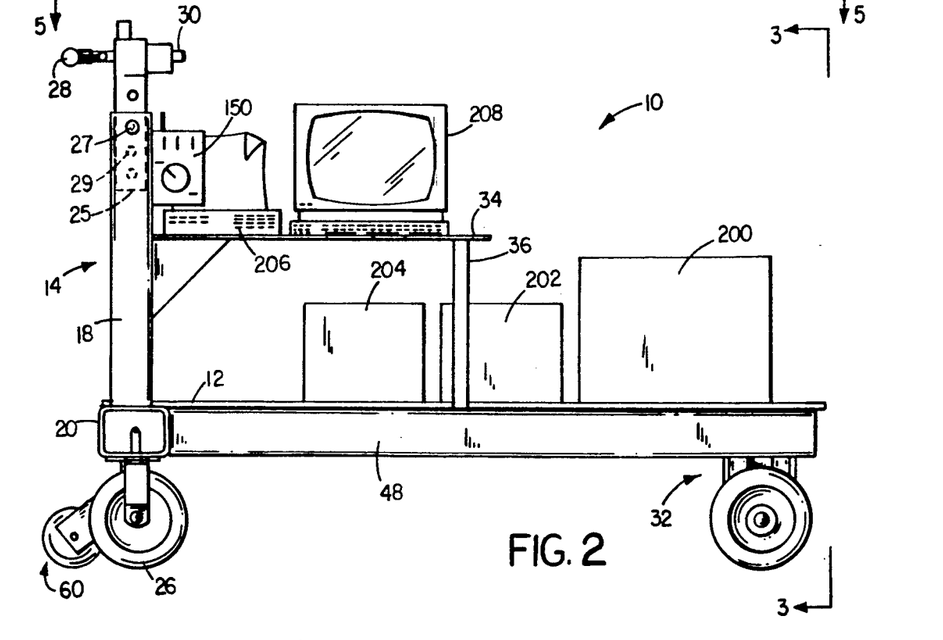

Referring to FIGS. 1 and 2, a four-wheeled cart 10 for simulating physical work is provided with a horizontal planar base 12 attached substantially perpendicular to a vertical frame 14. Frame 14 is formed from two substantially parallel hollow vertical tubes 16, 18, each having a substantially square cross-section, joined to opposite ends of a horizontal lower member 20. A horizontal upper member 22 is attached to two substantially parallel vertical tubes 23, 25 each having a substantially square cross-section sized to telescopically fit into vertical tubes 16, 18 respectively. The telescoping vertical tubes are secured by pins 27 which pass through aligned holes 29 in each of the telescoping tube pairs. Vertically distributed holes in the vertical tubes allow the height of the upper member to be varied by simply pinning those holes which align at the desired height. Upper member 22 has a handle 28 disposed substantially parallel to the upper member and attached by parallel handle guides 30 which slidably ride on ball bushings 33 (commercially available from Thomson, Thomson, Conn., part number A-101824), mounted in upper member apertures 31. The ball bushings assure that the handle guides slide freely with respect to the upper member, as well as the rest of the cart.

Cart base 12 is supported on one end by horizontal lower member 20, and along its length by a central support beam 48 of substantially rectangular cross-section. One end of central support beam 48 is welded to horizontal lower member 20, and the other end is supported by a front two-wheel assembly 32. Horizontal lower member 20 has a rear wheels 24, 26 mounted on each end. The rear wheels are free wheeling and mounted on a swivel allowing 360 degrees of directional rotation. A directional wheel assembly 60 is mounted on horizontal lower member 20 centered between the two rear wheels to indicate the direction of the cart, as discussed below.

An equipment shelf 34 is disposed horizontally and parallel to base 12 and is supported on one end by vertical members 16, 18, and on the other end by two vertical shelf supports 36 (one shown) between the shelf and the base.

Figure 3:
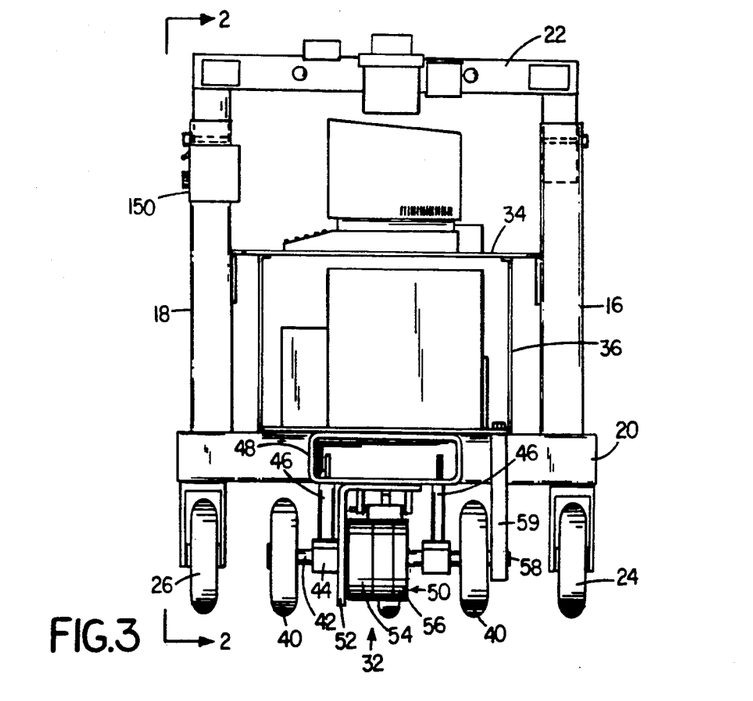

Referring to FIG. 3, front wheel assembly 32 has two wheels 40 fixedly mounted on each end of an axle 42 which is rotatably mounted through two pillow blocks 44 supported by pillow block supports 46. Pillow block supports 46 are rigidly attached to support member 48 connected to the bottom surface of cart base 12. Axle 42 also passes through an electromagnetic brake assembly 50 disposed between pillow blocks 44. A brake mounting plate 52 perpendicularly extends from central support beam 48 to rigidly support and prevent rotation of the fixed portion of the brake assembly.

Electromagnetic brake assembly 50 (commercially available from Electroid, Springfield, N.J., part number EC42B-12) has a rotary brake portion 56 fixedly attached to axle 42, and an adjacent fixed brake portion 54 fixedly attached to brake mounting plate 52. Electrical current applied to the fixed brake portion creates a magnetic field which inhibits the free rotation of the adjacent rotary brake portion attached to the axle, and thereby creates resistance to the rotation of front wheels 40. Adjustment of the electrical current applied to the fixed brake portion determines the amount of force required to rotate the front wheels, and thus determines the amount of force required to push the cart.

A tachometer 58 (commercially available from Electromatic Equipment Co., Cedarhurst, N.Y., part number DT 5FV #73028807) is mounted adjacent to one of front wheels 40 by means of a tachometer sensor mounting block 59 attached to base 12. Tachometer 58 senses the rotation of the adjacent wheel to produce an electrical output indicative of the velocity of the cart.

Figure 4:
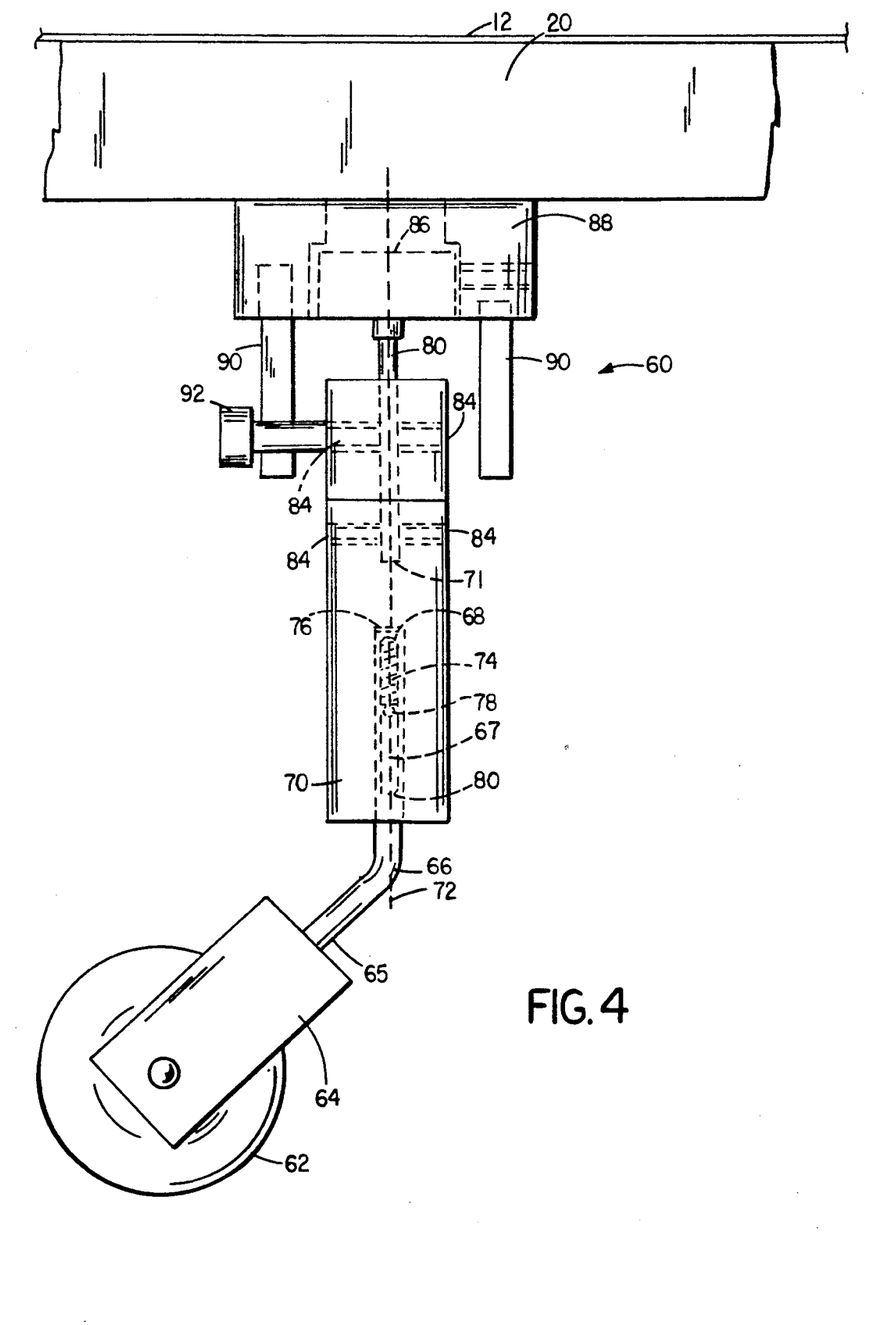
FIG. 4 is a side view of a direction indicator used with the cart shown in FIG.

Referring to FIG. 4, direction indicator wheel assembly 60 has a wheel 62 rotatably mounted in a wheel mount 64 attached to one end 65 of an angled member 66. The other end 67 of angled member 66 is accepted in a bore 68 in one end of a cylindrical support member 70 coaxial with the long axis 72 of the support member. End 67 of angled member 66 passes through a spring 74 which is captured between the closed end 76 of the bore and a spring pin 78 extending perpendicularly from the angled member. Spring pin 78 rides in a guide notch 80 adjacent to bore 68 to restrict the travel of angled member 66 along long axis 72 and prevent the angled member from rotating about the long axis relative to the cylindrical support member, thus causing both angled member 66 and cylindrical support member 70 to rotate in unison.

The other end of cylindrical support member 70 has a bore 71 coaxial with long axis 72 which accommodates one end of a potentiometer shaft 80. The potentiometer shaft is fixedly mounted in the bore by two sets of opposing set screws 84 threadably engaged with the cylindrical support member so the potentiometer shaft and the cylindrical support member rotate in unison about the long axis. The other end of the potentiometer shaft is connected to a potentiometer 86 (commercially available from Allen-Bradley, Fairfield, N.J., part number JA1N200P-5K) which is fixedly mounted in potentiometer block 88 attached to horizontal lower member 20. The potentiometer produces an electrical resistance indicative of the relative rotational position of the cylindrical support member to the cart base. The extent of rotation of the cylindrical support member is limited to approximately 180 degrees by a swivel stop 92 extending perpendicularly from the support member. Swivel stop 92 contacts travel stops 90 which extend from the potentiometer block and positioned at the rotational limits, and is thereby prevented from further rotation in each direction.

Angled member 66 is bent at an angle of approximately 30 degrees with respect to long axis 72 which is designed to cause wheel 62 to trail in the direction the cart is being turned. This in turn rotates cylindrical support member 70 relative to cart base 12 causing potentiometer 86 to produce a resistance value indicative of the direction of the cart. Spring 74 urges the wheel against the surface on which it is riding to help it track the surface, especially where the surface is rough, and reduces erroneous directional indications from the potentiometer.

Figure 5:
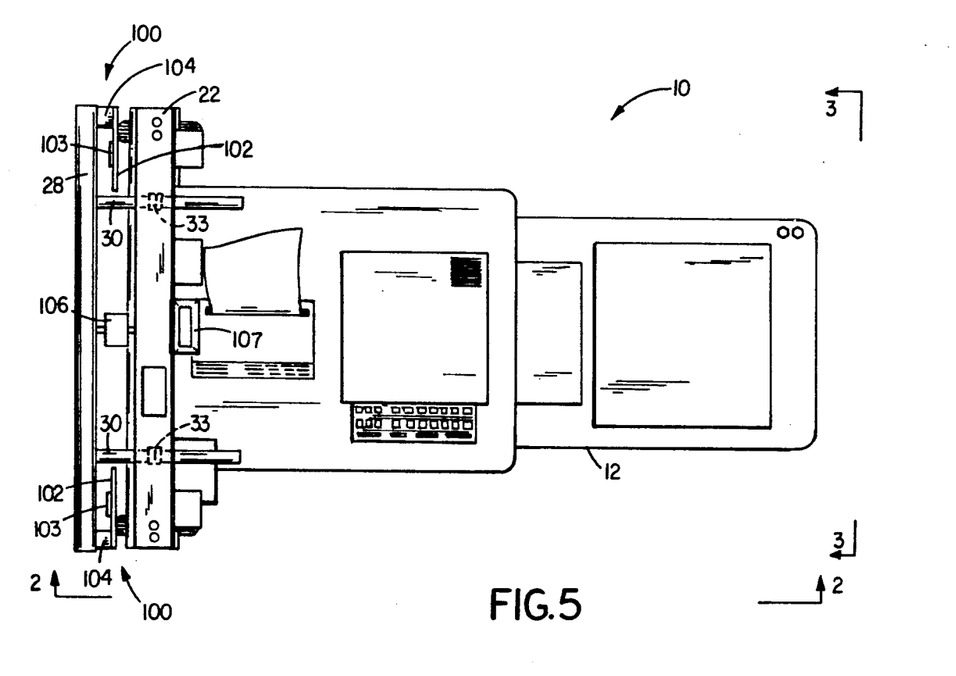
FIG. 5 is a top view of the cart shown in FIG. 1.

Referring to FIG. 5, handle 28 incorporates grip pressure sensors 100 on opposing ends of the handle between the handle and upper horizontal member 22. Each grip mount 100 has an elastic measurement beam 102 disposed substantially parallel to the handle. The beam has one end free and the other end attached to a mounting block 104 connected to the handle. A strain gauge 103 (commercially available from Baldwin Lyman Hamilton, Canton, Mass., FAE-12-25-56) is mounted on the surface of each elastic beam 102 so that simultaneous gripping of the handle and the elastic beam causes the strain gauge to produce an electrical signal indicative of the gripping force applied (i.e., the strain gauge measures the bending of the beam which is proportional to the gripping force applied to bend it).

Handle 28 also incorporates a load cell 106 (commercially available from Baldwin Lyman Hamilton, Canton, Mass., part number 461630) attached between the handle and upper horizontal member 22. Since parallel handle guides 30 are slidably engaged with the upper horizontal member, as described with reference to FIGS. 1 and 2, all pushing and pulling forces applied to the handle to move the cart are transferred to the upper horizontal member through the load cell. The electronic sensor within the load cell produces an electrical signal indicative of the pushing or pulling force applied to the handle and transferred to the cart. Additionally, the electrical signal from the load cell is connected to a direct reading digital millivolt meter 107 (commercially available from Simpson, Norwood, Mass., part number 24101) attached to horizontal member 22 to provide visual readback of the pushing and pulling forces applied to the handle.

Figure 6:
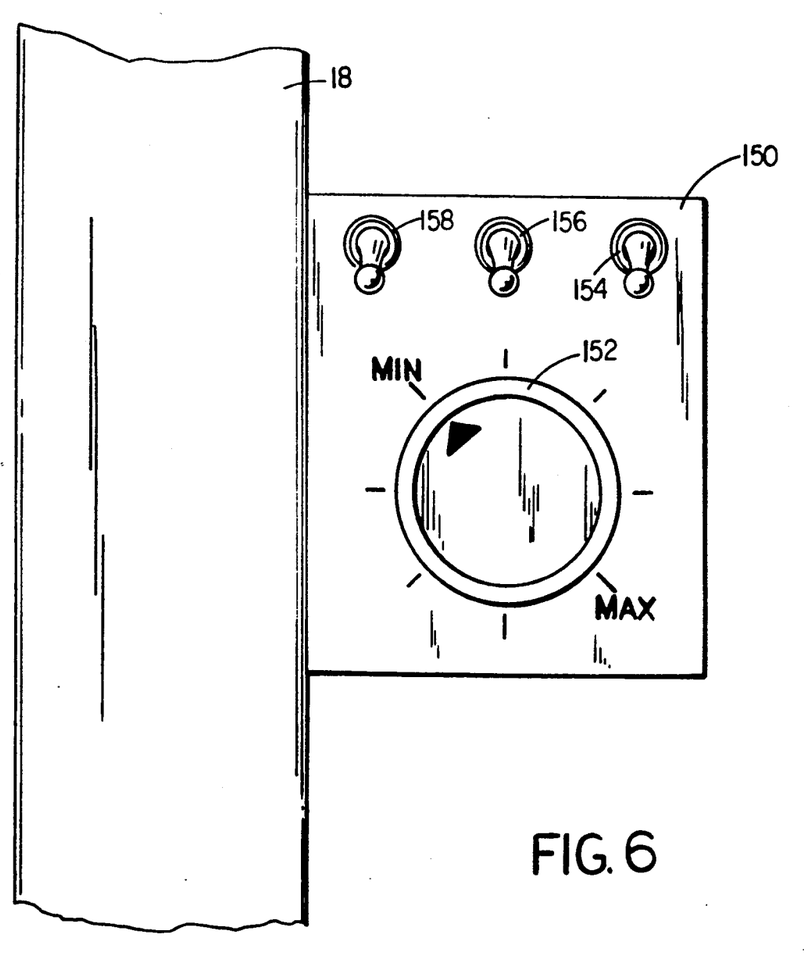
FIG. 6 is a front view of a control panel used with the cart shown in FIG. 1.

Referring to FIG. 6, a control panel 150 is attached to vertical member 18 (see FIG. 1) to provide a user controllable interface to several of the electrical devices on the cart. A rheostat 152 (commercially available from Allen-Bradley, Fairfield, N.J., part number 1712,) electrically connected to the fixed portion 54 of the electromagnetic brake (FIG. 3) allows the user to vary the electrical current supplied to the brake, and thus set the resistive forces encountered while pushing the cart. A battery switch 154 supplies power to the electrical devices on the cart from an onboard battery, discussed below. meter switch 156 is electrically connected to digital load meter 107 to turn the meter on and off. A grip switch 158 is electrically connected to the grip pressure sensors 100 to activate or deactivate them.

Referring again to FIG. 2 a rechargeable battery 200 (commercially available from Sears Roebuck and Company, Chicago, Ill., part number 27F) supplies power to various electrical devices on the cart. A battery charger 202 (commercially available from Sear Roebuck and Company, part number 2V-20A), is connected to the battery and may be plugged into electrical mains to recharge the battery between cart uses. A direct current to alternating current (DC-AC) invertor 204 (commercially available from Powerverter, Chicago, Ill., TRIPP LITE, Model-550) is connected to the battery and supplies alternating current to those electrical devices on the cart requiring it.

A DC powered data logger 206 (commercially available from Hewlett Packard, Palo Alto, Calif., part number 160B) disposed on equipment shelf 34 accepts electrical signals from the various sensors positioned about the cart, specifically, cart velocity tachometer 58, cart direction potentiometer 86, both grip sensor strain gauges 104, and push-pull force load cell 106. Each signal is applied to a separate data logger input channel which is sampled by the data logger approximately once a second and collected in the data logger's internal memory. The collected data are then downloaded from the data logger to a personal computer 208 through an RS232 data link as an ASCII file. The personal computer contains "standard" software programs (e.g., Lotus 123, data bases, e.g., DBASE IV, for processing, analyzing, comparing and reporting the results of the test performed.

Operation

Before a test is run and a set of measurements gathered, the cart must be configured for the individual subject and the type of test desired. The height of handle 28 (FIG. 1) is adjusted using pins 27 to attain the desired anthropomorphic conditions (i.e., to simulate job performance based on the physical characteristics of the job in relation to the physical characteristics of the subject). Battery power switch 154 (FIG. 6) is turned on to activate the onboard electronic equipment. Electromagnetic brake rheostat 152 is adjusted to provide the desired cart push and pull resistance. Data logger 206 is activated and the test is begun.

Figure 7:
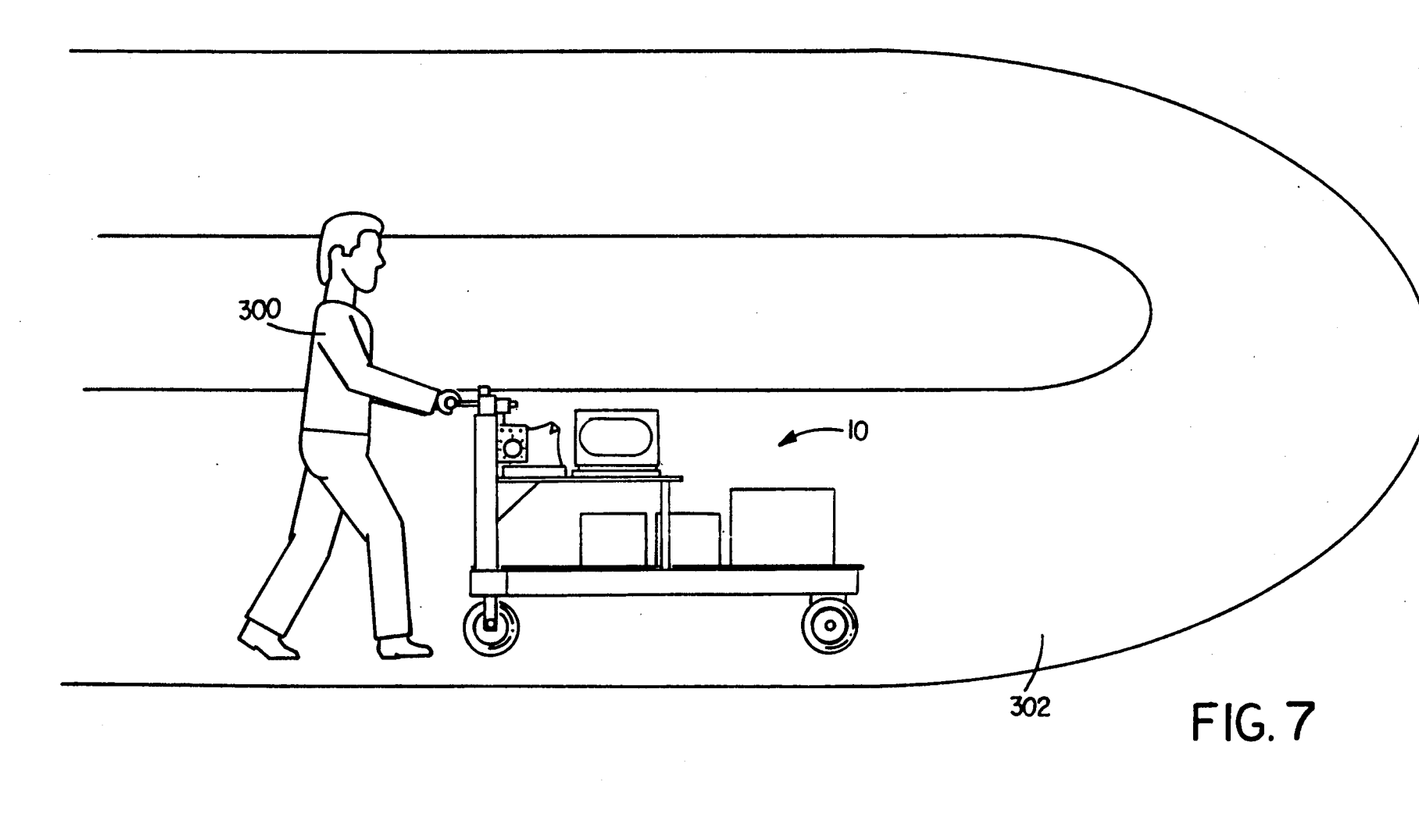
FIG. 7 is a perspective view of the cart during use in a method of this invention.

Referring to FIG. 7, a subject 300 of the test grips the handle and pushes or pulls the cart through a predetermined sequence of maneuvers over straight, inclined, and curved paths along a test track 302. The data logger accumulates data samples from the various sensors around the cart representing push and pull forces, cart velocity, cart direction and handle grip forces. The data logger allows the test operator to mark each set of data so that it may be identified and correlated with the test conditions incident to that particular data set (i.e., handle height, brake resistance, track conditions, maneuver type). After a predetermined set of maneuvers is run the data are transferred to the personal computer for further analysis.

Testing Methods

This invention allows dynamic testing of subjects to quantitatively evaluate extremity functions. In particular the cart of this invention simultaneously measures dynamic forces characteristic of extremity function, including push and pull forces required to move the cart along straight paths, turning forces required to move the cart around a curve, cart acceleration forces, cart jerk forces (rate of change of acceleration), cart velocity, and grip strength.

A variety of independent variables may be input into the test through manipulation of the cart brake parameters and the inclination and path of the track. For instance, after measuring a subject's maximal isometric effort through traditional means, the cart brake resistance and track conditions (i.e., inclination, curves, surface texture) may be adjusted to test the subject at some percentage of the measured maximal isometric effort (i.e., 25% or 50%). Testing at submaximal isometric effort levels help to prevent injury to the subject and make it more difficult for the subject to feign a disability. Additionally, the handle can be adjusted to simulate a variety of anthropomorphic conditions.

The various sensors on the cart collect a variety of measurements characteristic of a subject's physical ability. These measurements are gathered by the data logger and sent to the computer for further analysis including comparison of the measurements with normal and abnormal control groups, and with the subject's past performance. The measurements provide data for calculating a set of dependent variables including peak force, average force, velocity, displacement, acceleration, jerk (rate of change of acceleration), and endurance for any particular task.

Of particular interest is the determination of the sincerity of effort of the subject during exercise, which may be relevant to evaluating workman's compensation and other injury claims. The measurement of grip strength during pushing, pulling and turning can be indicative of the sincerity of effort since it is difficult for the subject to control. Additionally, it may not be apparent to the subject that grip strength measurements are being recorded, and thus the subject may not think, or know, to adjust his grip to be consistent with the remainder of the test results.

A typical test protocol involves the subject executing a sequence of maneuvers with the cart around a test track. The test subject is first measured for isometric strength and the brake on the cart is set to provide a pushing resistance of approximately 25% of the maximal isometric strength measured From a start point the subject pushes the cart along a predetermined path including a straight portion and a curved portion. The subject then pulls the cart back along a predetermined straight path The brake on the cart is then adjusted to provide a pushing resistance of approximately 50% of the maximal isometric strength measured. The subject then repeats the same pushing and pulling sequence. The subject is measured again for isometric strength and the above test is repeated using the new maximal isometric strength measurements.

Other embodiments are within the following claims.

I claim:

1. A dynamic physiological function measurement mobile apparatus, comprising
   a mobile structure comprising a frame and a plurality of wheels and a handle disposed on said frame, and being of a size and weight for manual propulsion by a human;
   a brake attached to at least one of said wheels for controlling the amount of force required for a human to move said structure, said brake permitting human propulsion, thereby simulating the force exerted by a human during a task; and
   a directional sensor attached to said structure for indicating the direction in which said structure is moving.

2. The mobile apparatus of claim 1 further comprising a velocity sensor attached to said structure for indicating the velocity of said structure.

3. The mobile apparatus of claim 1 further comprising at least one grip sensor on said handle for measuring gripping force applied to said handle.

4. The mobile apparatus of claim 1 further comprising
   a velocity sensor attached to said structure for indicating the velocity of said structure; and
   at least one grip sensor on said handle for detecting gripping force applied to said handle.

5. The mobile apparatus of claim 1, 2, 3 or 4 wherein said directional sensor comprises
   a wheel for contacting the surface on which said structure is moving;
   an angled member connected on one end to said wheel; and
   a potentiometer having a body fixedly connected to said structure and a rotatable shaft connected to the other end of said angled member, said potentiometer producing an electrical resistance indicative of the relative rotation of said shaft to said structure.

6. A dynamic physical function measurement mobile apparatus, comprising
   a mobile structure comprising a frame and a plurality of wheels and a handle disposed on said frame, and being of a size and weight for manual propulsion by a human;
   a brake attached to at least one of said wheels for controlling the amount of force required for a human to move said structure; and
   at least one grip sensor on said handle for measuring gripping force applied by a human to said handle as said human moves said structure.

7. The mobile apparatus of claim 6 further comprising a velocity sensor attached to said structure for indicating the velocity of movement of said structure.

8. The mobile apparatus of claim 3, 4, 6, or 7 wherein said grip sensor comprises
   an elongated elastic beam spaced from and substantially parallel to said handle; and
   a strain gauge attached to said beam to measure the bending of said beam toward said handle.

9. A dynamic function measurement mobile apparatus, comprising
   a mobile structure comprising a frame and a plurality of wheels and a handle disposed on said frame, and being of a size and weight for manual propulsion by a human;
   a brake attached to at least one of said wheels for controlling the amount of force required for a human to move said structure; and
   a velocity sensor attached to said structure for indicating the velocity of said structure during human propulsion.

10. The mobile apparatus of claim 1, 2, 3, 4, 6, 7, or 9 further comprising
    a force sensor attached between said handle and said frame for indicating the amount of force applied to said handle to push or pull said structure.

11. Mobile apparatus of claim 1, 2, 3, 4, 6, 7, or 9 wherein said brake comprises
    a rotary portion connected to said wheel; and
    a fixed portion adjacent said rotary portion and connected to said structure for applying a variable resistance force to the rotation of said rotary portion.

12. The mobile apparatus of claim 11 wherein
    said fixed portion comprises an electromagnet providing a magnetic force; and
    said rotary portion is responsive to said magnetic force.

13. The mobile apparatus of claim 1, 2, 3, 4, 6, 7, or 9 wherein said brake comprises an electromagnetic brake having a variable resistance responsive to the amount of electrical energy applied to said brake.

14. The mobile apparatus of claim 1 further comprising
    a data logger connected to said directional sensor for recording an indication from said directional sensor.

15. The mobile apparatus of claim 14 further comprising
    a computer connected to said data logger for accepting said recorded indication from said data logger.

16. A dynamic physiological function mobile apparatus, comprising:
    a mobile structure comprising a frame and a plurality of wheels and a handle disposed on said frame;
    a brake attached to at least one of said wheels for controlling the amount of force required by a human to move said structure;
    a directional sensor attached to said structure for indicating the direction in which said structure is moving;
    a velocity sensor attached to said structure for indicating the velocity of said structure; and
    at least one grip sensor on said handle for measuring gripping force applied to said handle.

17. The mobile apparatus of claim 2, 4, 7 or 9 further comprising
    a data logger connected to said velocity sensor for recording an indication from said velocity sensor.

18. The mobile apparatus of claim 3, 4 or 6 further comprising
    a data logger connected to each said grip sensor for recording an indication from each said grip sensor; and
    a data logger connected to said velocity sensor for recording an indication from said velocity sensor.

19. The mobile apparatus of claim 4 further comprising
    a data logger connected to each said grip sensor for recording an indication from each said grip sensor; and
    a data logger connected to said velocity sensor for recording an indication from said velocity sensor.

* * * * *